(12) United States Patent  
Hauri

(10) Patent No.: US 8,029,463 B2  
(45) Date of Patent: Oct. 4, 2011

(54) NEEDLE PROTECTION ASSEMBLY

(75) Inventor: Marius Hauri, Westmoreland, NH (US)

(73) Assignee: Smiths Medical ASD, Inc., Keene, NH (US)

( * ) Notice: Subject to any disclaimer, the term of this patent is extended or adjusted under 35 U.S.C. 154(b) by 377 days.

(21) Appl. No.: 11/712,939

(22) Filed: Mar. 2, 2007

(65) Prior Publication Data  
US 2007/0156088 A1    Jul. 5, 2007

Related U.S. Application Data

(62) Division of application No. 10/649,837, filed on Aug. 28, 2003, now Pat. No. 7,201,736.

(51) Int. Cl.  
A61M 5/00 (2006.01)

(52) U.S. Cl. .................. 604/110; 604/263; 604/192

(58) Field of Classification Search .............. 604/110, 604/192, 240, 263, 187  
See application file for complete search history.

(56) References Cited

U.S. PATENT DOCUMENTS

| 4,664,259 A | 5/1987 | Landis |
| 4,931,048 A * | 6/1990 | Lopez ........................... 604/110 |
| 4,982,842 A | 1/1991 | Hollister |
| 5,037,401 A | 8/1991 | DeCamp |
| 5,139,489 A | 8/1992 | Hollister |
| 5,154,285 A | 10/1992 | Hollister |
| 5,171,303 A | 12/1992 | DeCamp |
| 5,188,611 A | 2/1993 | Orgain |
| 5,232,454 A | 8/1993 | Hollister |
| 5,277,311 A | 1/1994 | Hollister |
| 5,490,841 A * | 2/1996 | Landis ........................... 604/110 |
| 5,509,907 A | 4/1996 | Bevilacqua |
| 5,584,816 A * | 12/1996 | Gyure et al. .................. 604/192 |
| 5,599,313 A | 2/1997 | Gyure et al. |
| 5,599,318 A | 2/1997 | Sweeney et al. |
| 5,632,732 A | 5/1997 | Szabo et al. |
| 5,662,617 A | 9/1997 | Odell et al. |
| 5,665,075 A | 9/1997 | Gyure et al. |
| 5,669,889 A * | 9/1997 | Gyure et al. .................. 604/263 |
| 5,681,295 A | 10/1997 | Gyure et al. |
| 5,697,908 A | 12/1997 | Imbert et al. |
| 5,733,265 A | 3/1998 | Bachman et al. |
| 5,746,726 A | 5/1998 | Sweeney et al. |
| 5,868,716 A | 2/1999 | Sweeney et al. |
| 5,891,103 A | 4/1999 | Burns |
| 5,913,846 A | 6/1999 | Szabo |
| 5,919,165 A | 7/1999 | Benson |
| 5,993,426 A | 11/1999 | Hollister |
| RE37,110 E | 3/2001 | Hollister |
| RE37,252 E | 7/2001 | Hollister |

(Continued)

Primary Examiner — Theodore Stigell  
Assistant Examiner — Laura Schell  
(74) Attorney, Agent, or Firm — Louis Woo

(57) ABSTRACT

A needle protection assembly has a needle hub with a proximal portion having two sets of spaced flanges and a distal portion having a number of arms for forming at least one catch and one slot. A collar with a needle protection housing has at its inner surface a number of protrusions fittable within the space defined by the two sets of flanges, when the collar is press-fitted to the needle hub, and a number of fingers that removably grasp a needle sheath that covers the needle extending from the needle hub. After the sheath is removed, the needle protection housing may be pivoted to cover the needle. Once the housing fully covers the needle, a spline inside the housing coacts against the catch at the needle hub to enable the needle hub to be removed from a syringe by rotating the housing.

21 Claims, 7 Drawing Sheets

U.S. PATENT DOCUMENTS

| | | |
|---|---|---|
| 6,328,713 B1 | 12/2001 | Hollister |
| 6,440,104 B1 | 8/2002 | Newby et al. |
| 6,719,737 B2 | 4/2004 | Kobayashi |
| 7,156,825 B2 * | 1/2007 | Hudon .......................... 604/192 |
| 2003/0078548 A1 * | 4/2003 | Kobayashi .................... 604/263 |
| 2003/0212369 A1 * | 11/2003 | Kobayashi .................... 604/197 |

* cited by examiner

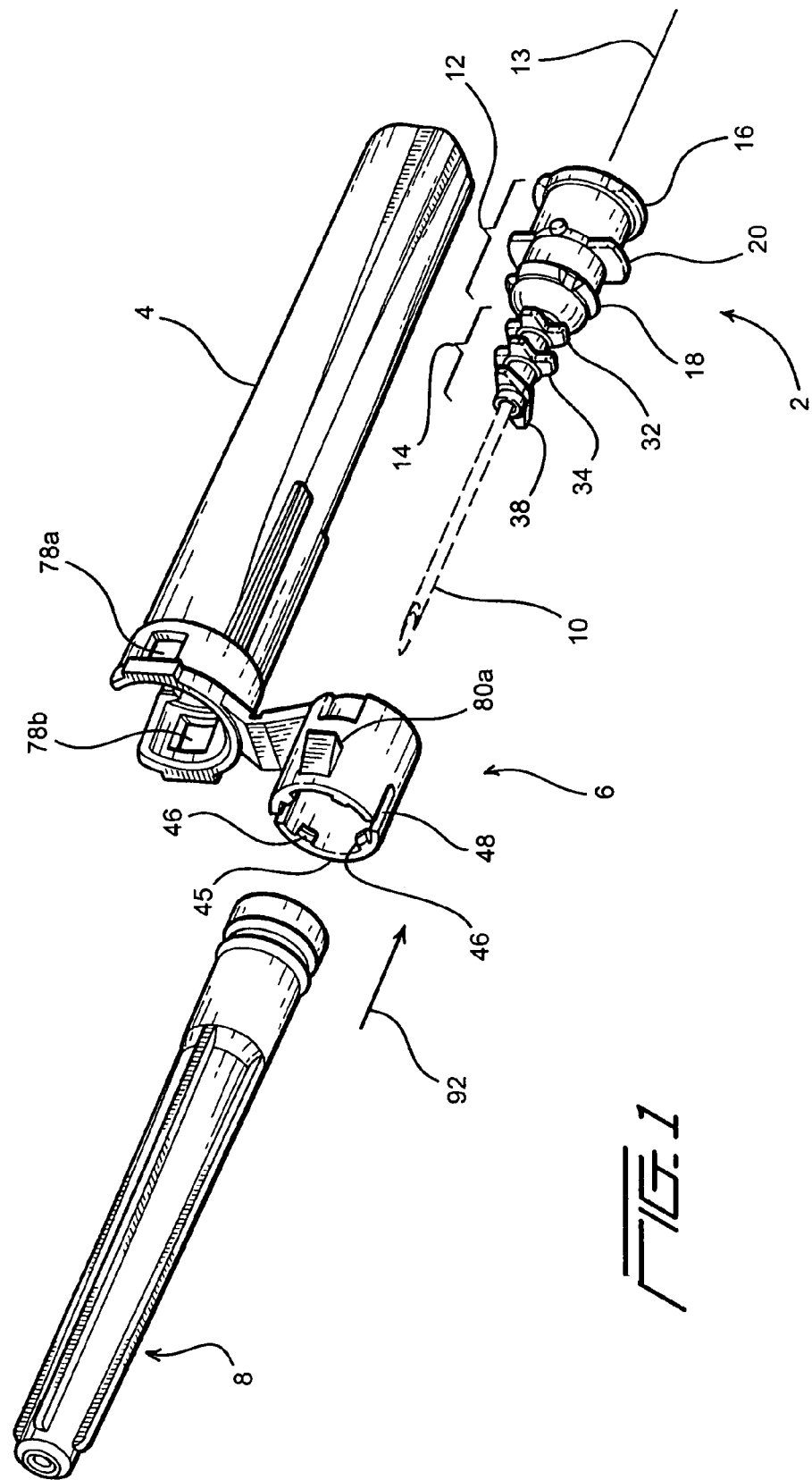

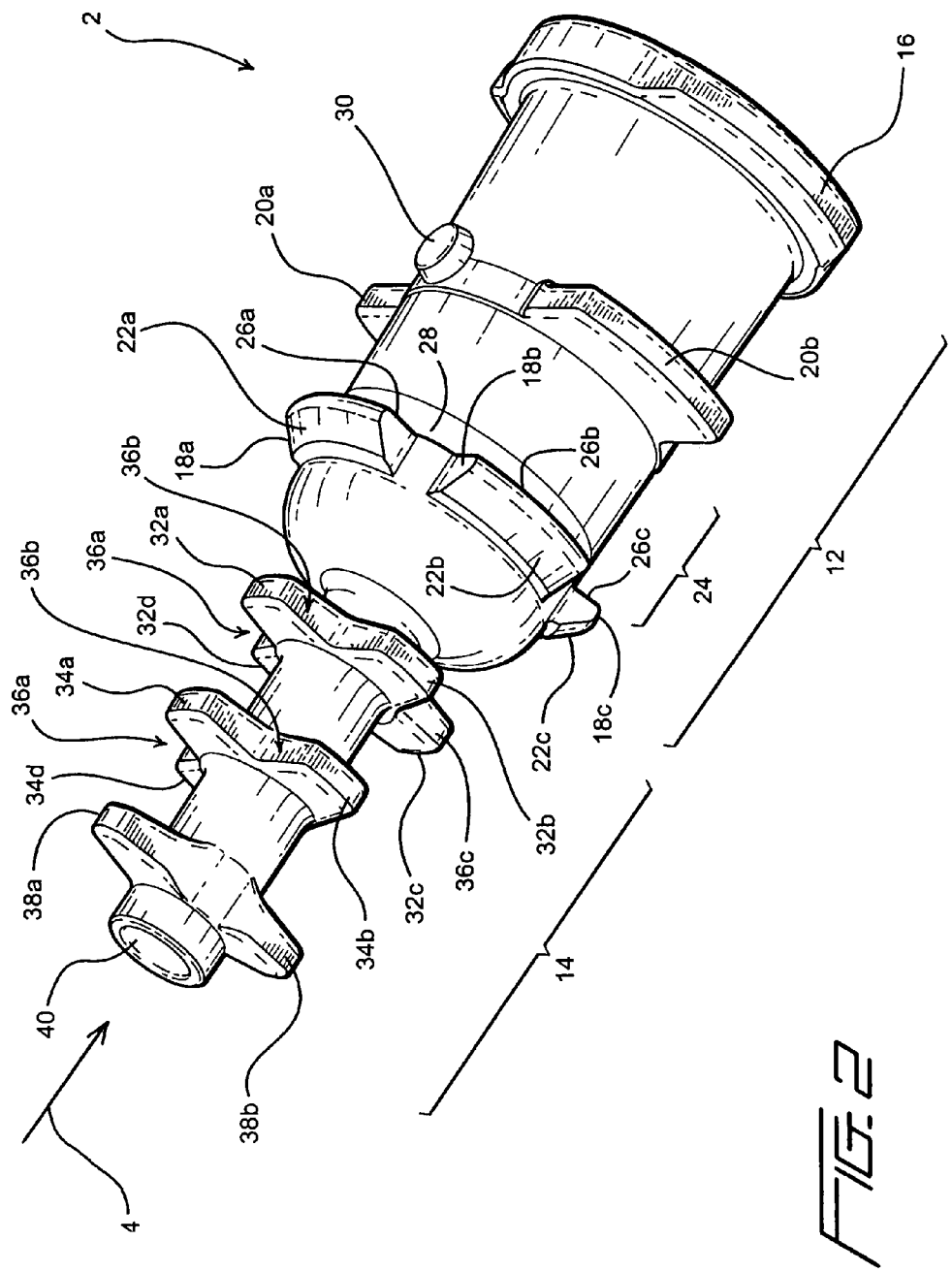

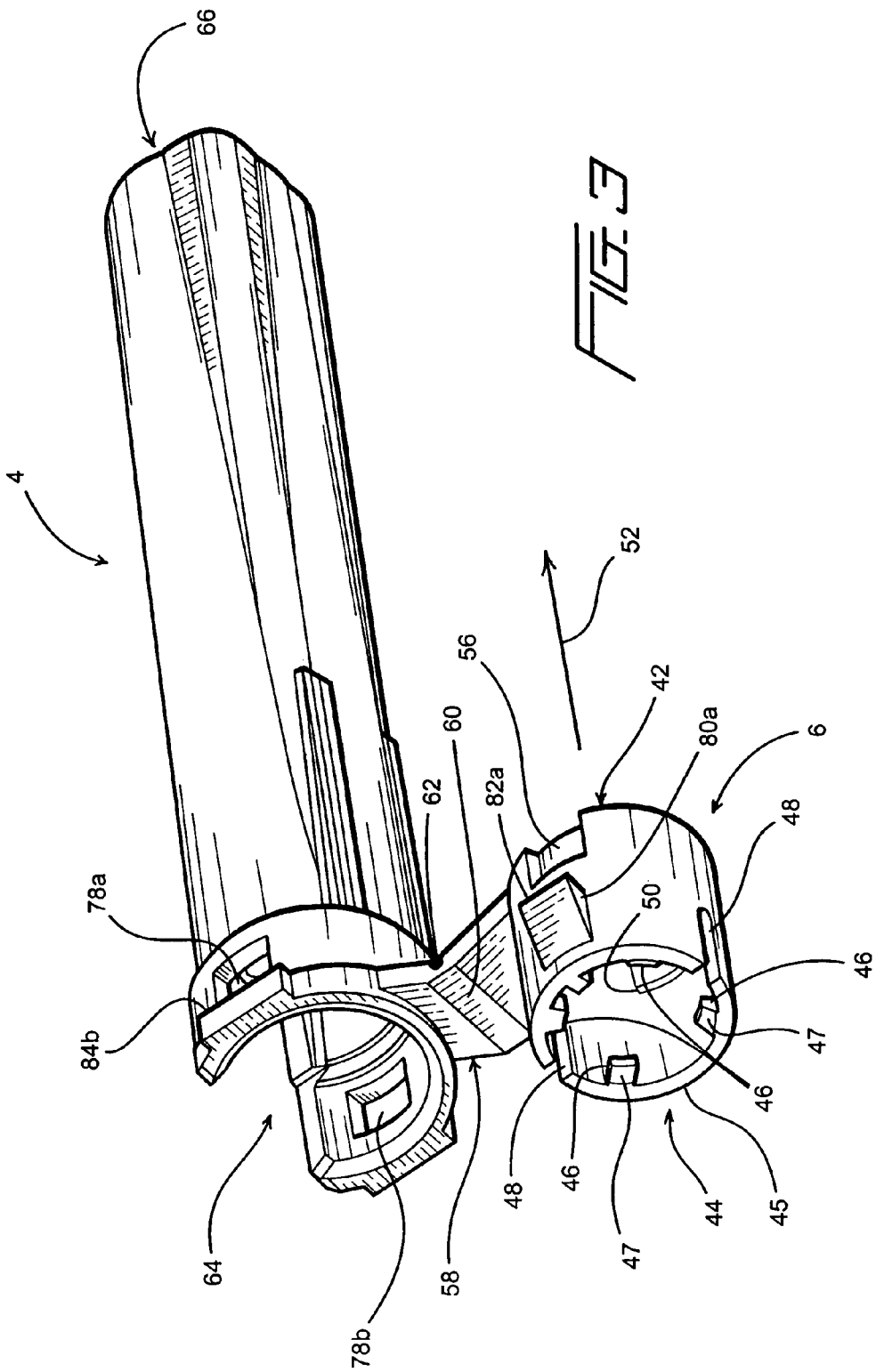

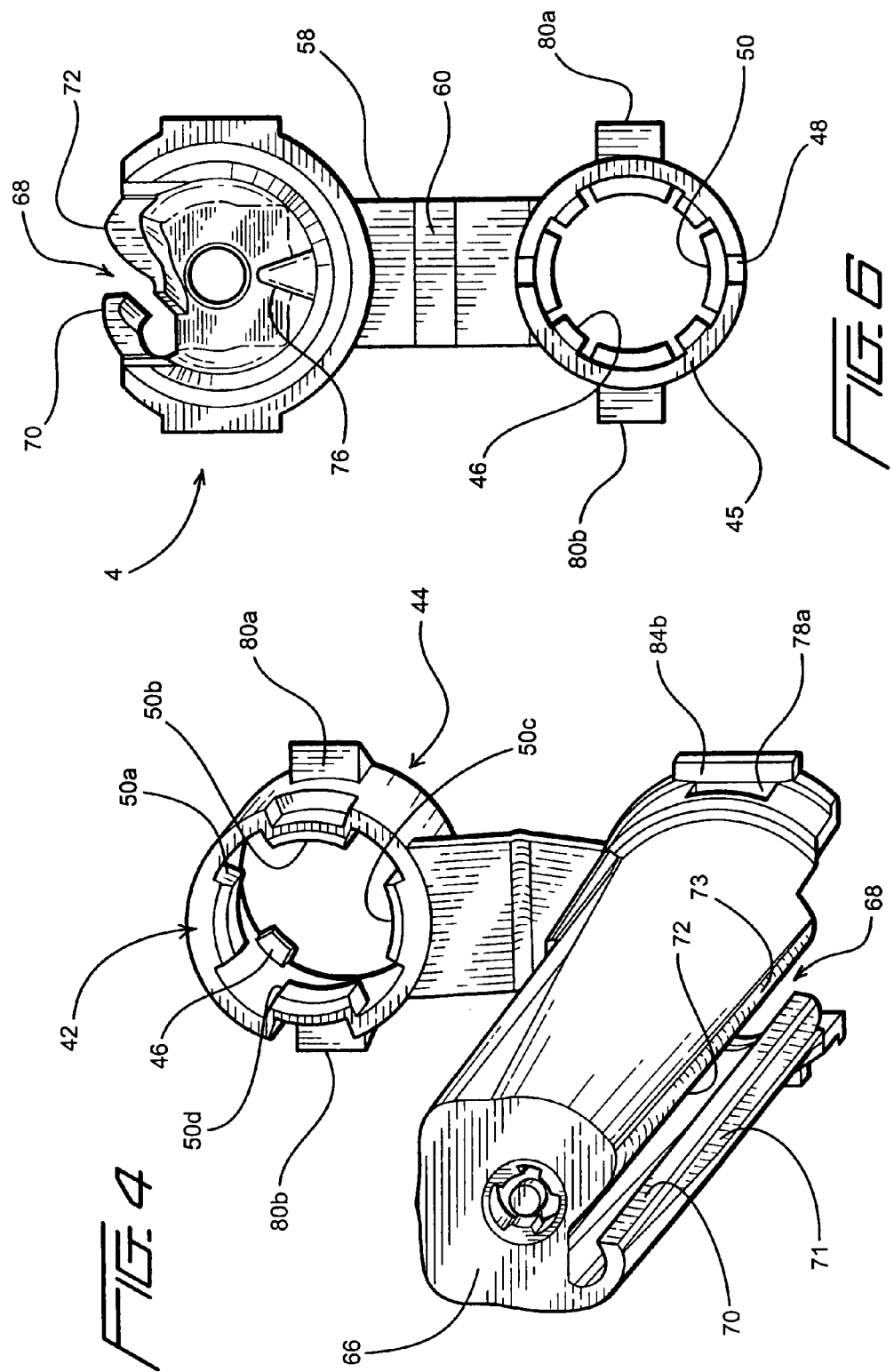

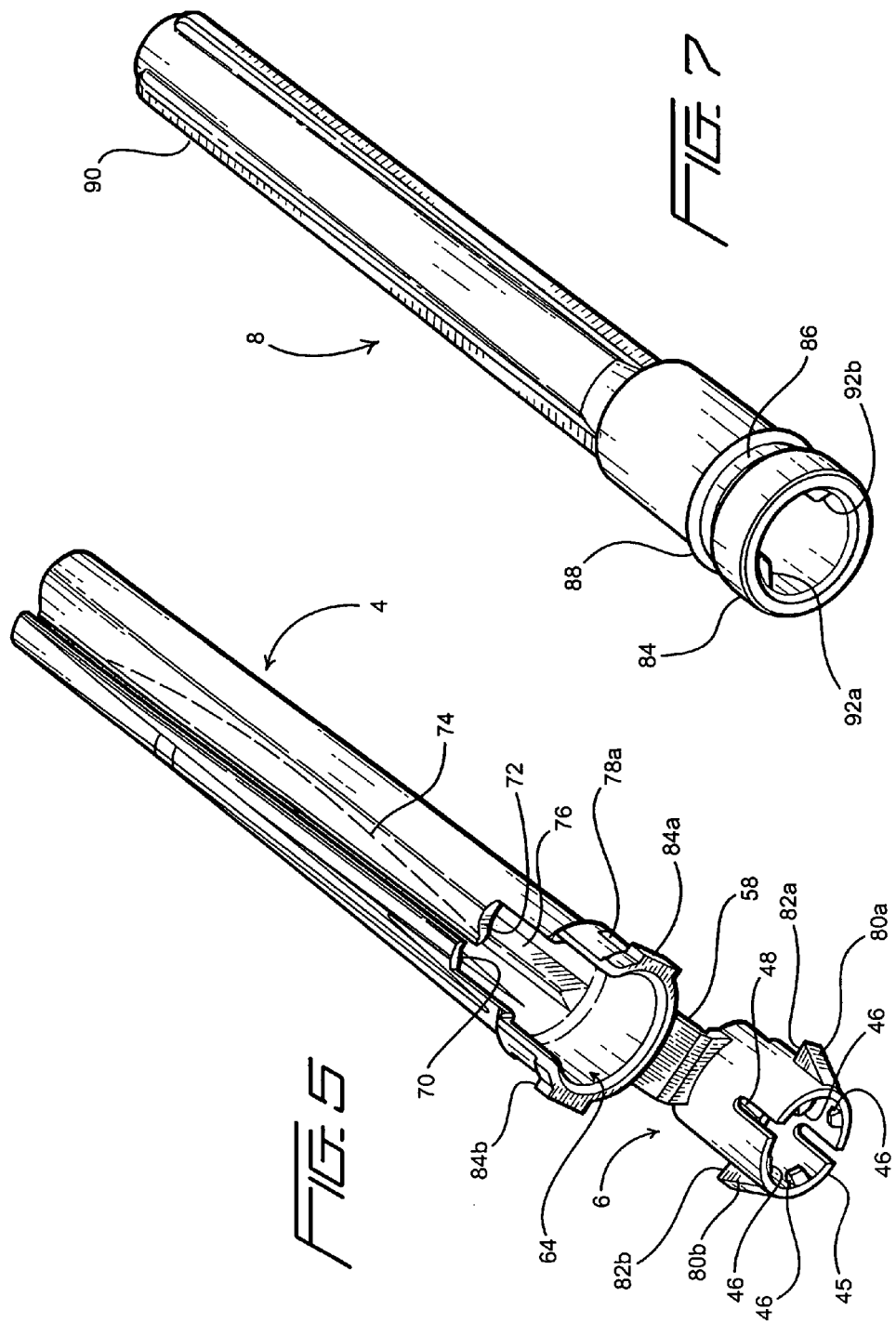

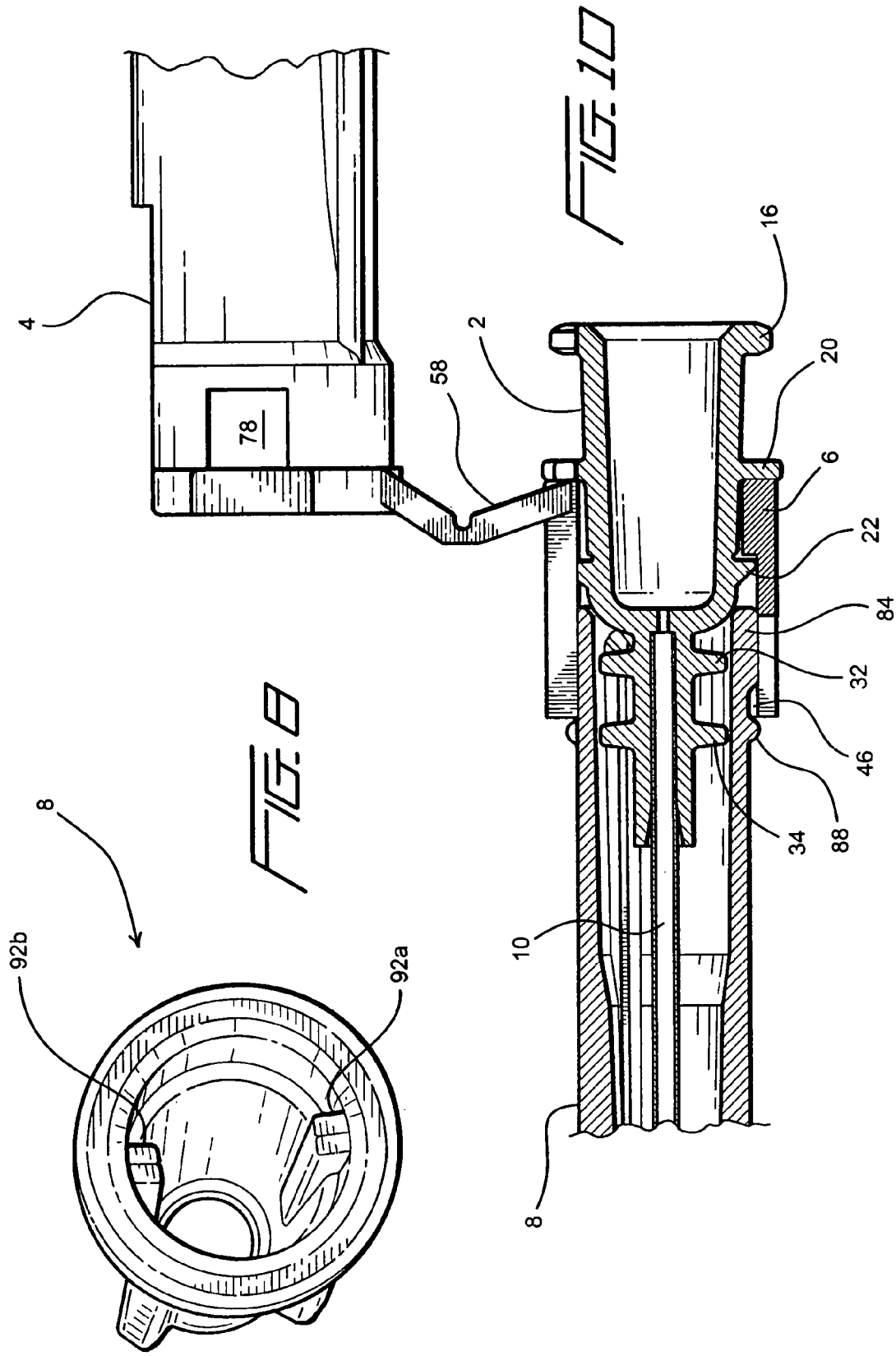

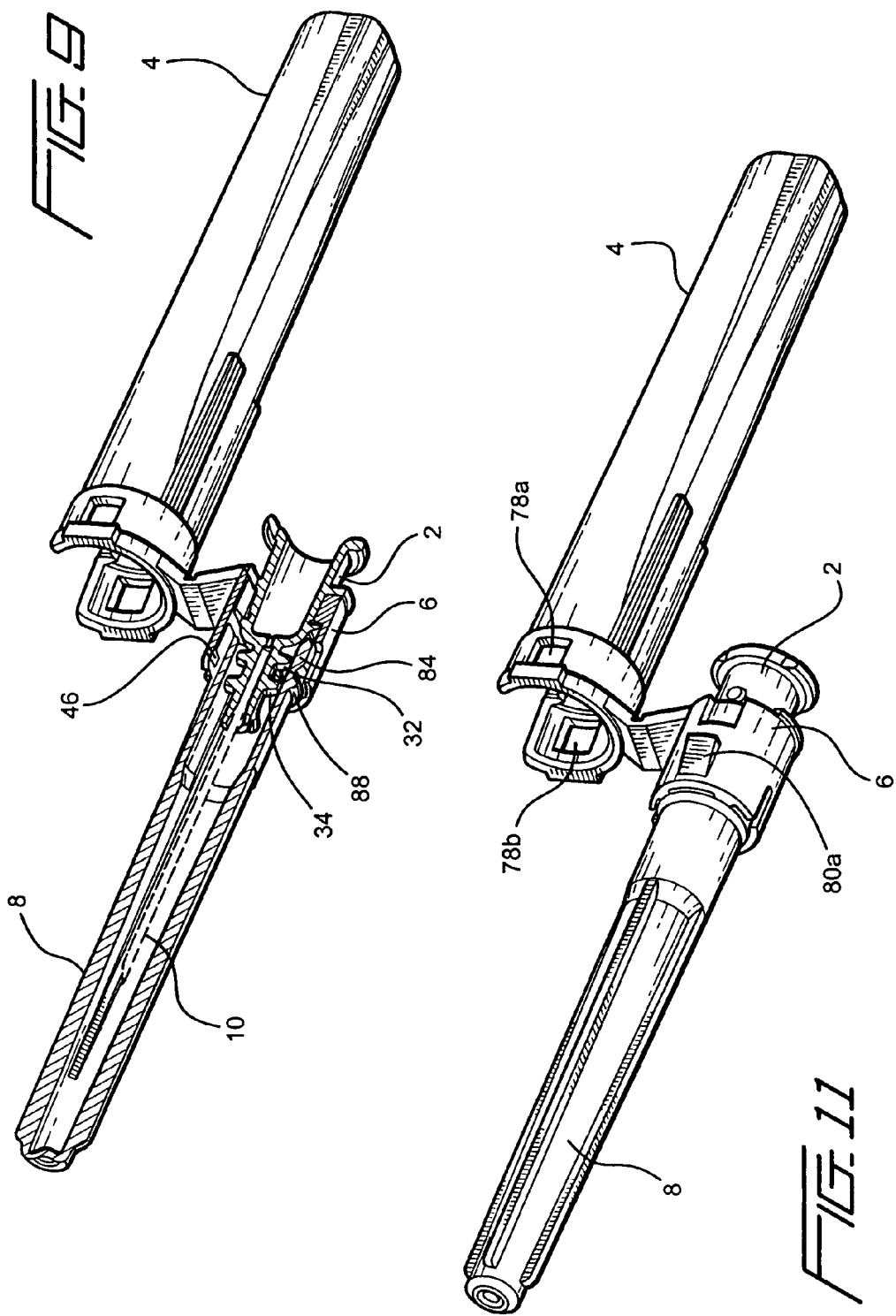

NEEDLE PROTECTION ASSEMBLY

This application is a divisional of application Ser. No. 10/649,837, filed on Aug. 28, 2003, now U.S. Pat. No. 7,201,736.

FIELD OF THE INVENTION

The present invention relates to needles and more particularly a needle protection assembly in which the needle is first protected by a needle sheath prior to use, and protected after use by a housing.

BACKGROUND OF THE INVENTION

There are a number of needle protection devices disclosed in the prior art. Among them are a number of patents assigned to the same assignee as the instant invention. Without limitations, some of those patents are: U.S. Pat. Nos. 4,982,842; 5,139,489; 5,154,285; 5,232,454; 5,277,311; 5,993,426; 6,328,713; 6,334,857; RE37,110 and RE37,252. Some other patents that describe needle protection devices, or parts thereof, include U.S. Pat. Nos. 4,664,259; 5,037,401; 5,171,303; 5,188,611; 5,490,841; 5,509,907; 5,584,816; 5,599,313; 5,599,318; 5,632,732; 5,643,219; 5,662,617; 5,665,075; 5,669,889; 5,681,295; 5,697,908; 5,733,265; 5,868,716; 5,891,103; 5,913,846; 5,919,165 and 6,440,104.

The needle protection assembly of the instant invention is made up of parts that are radically different from the prior art, as exemplified by the above-noted patents.

SUMMARY OF THE PRESENT INVENTION

The needle protection assembly of the instant invention has a specially designed needle hub that has a distal portion and a proximal portion. Provided at the proximal portion are two sets of flanges for defining a space onto which the collar of a needle protection housing is fitted. The respective sets of flanges may have different dimensions, with those flanges to which the collar is to be press-fitted being chamfered or beveled on the side that first meets the collar, so as to enable easy fitting of the collar onto the space defined by the flanges. The front flanges, assuming those are the beveled flanges, each have a back end that is formed to prevent the collar from being removed, once the collar is fitted past those front end flanges. The back end flanges provide a stop for the collar, so that, once the collar is fitted within the space, it will remain fitted thereat, although being rotatable about the body of the needle hub. At the distal portion of the needle hub there are a number of arms or stubs extending therefrom for forming at least one slot and at least one catch. A needle is attached to, and extends from, the distal end of the distal portion of the needle hub.

The collar to which a needle protection housing is connected comprises a proximal portion and a distal portion. There are a number of protrusions formed at the interior surface or wall of the collar at the proximal portion. The protrusions have dimensions that enable them to fit into the space defined by the flanges at the needle hub. The inherent elastic properties of the materials, such as ABS plastic or polypropylene, that made up the needle hub and the collar of the instant invention enable the collar, and more particularly the protrusions at the interior surface of the proximal portion thereof, to be press-fitted over the front flanges of the needle hub, so that the collar is rotatably mounted onto the space defined by the flanges about the needle hub.

At the distal portion of the collar there are a number of fingers, or catch members formed for removably retaining a needle sheath. Channels or slots are provided at the distal portion of the collar to enable the retention of the needle sheath to the collar for covering the needle from the needle hub before its use. The needle sheath is removed when the needle is to be used.

Connected to the collar by a hinge is a needle protection housing that has an open proximal end and a closed distal end. Formed substantially along the length of the housing is an opening that is off centered. The opening is formed by two lips or flaps that extend substantially along the length of the housing, with the first or upper lip overlapping the second or lower lip. The respective lips each are angled toward the interior of the housing, but with varying angles along the lengths of the lips. As a consequence, when the housing is pivoted to cover a used or contaminated needle, the needle would enter into the housing guided by the lips at angles that ensure that it smoothly enters into the housing. This prevents flickering of any contaminated fluid that may have adhered to the needle. The lips, particularly the lower lip, are designed such that, once fully enters into the housing, the needle is prevented from escaping from the housing. For added safety, respective portions of a locking mechanism are provided at the proximal portion of the housing and the outer surface of the distal portion of the collar.

Before use and for shipping purposes, a needle sheath is coupled to the collar, with the fingers at the distal portion of the collar gripping the proximal portion, or lower end, of the needle sheath where a rim is formed. Although securely held for shipping purposes to ensure that no accidental force would dislodge the needle sheath from the collar, the coupling of the needle sheath to the collar is designed to be removable so that when the needle is to be used, the needle sheath may be readily removed from the collar by the application of a predetermined force.

To mate the needle hub to a conventional syringe, the needle hub of the instant invention assembly may be directly inserted over a slip type luer. To thread the needle hub onto a luer lock end of a conventional syringe, at least one integral spline is provided at the inner wall of the needle sheath for coacting with a catch formed by a number of arms extending from the distal portion of the needle hub. Once the spline of the needle sheath makes contact with the catch at the distal portion of the needle hub, when the needle sheath is rotated, the needle hub likewise is rotated. Accordingly, the needle hub could be readily threaded onto a conventional luer lock end of a conventional syringe.

To remove the needle protection assembly of the instant invention from the syringe after use, an internal spline provided in the interior wall of the needle protection housing is used. When the housing is pivoted to cover the contaminated needle, as the needle enters into the housing, the internal spline of the housing will fit into a slot formed by some of the arms extending at the distal portion of the needle hub. Once thus fitted into the slot, when the housing is rotated, the needle hub likewise is rotated. Accordingly, once the needle is fully covered by the housing and it is desired to remove the needle protection assembly from the syringe, a user only needs to rotate the housing to remove the needle protection assembly from the syringe.

The needle protection assembly of the instant invention therefore includes a needle hub having a longitudinal axis and a needle extending from one of its ends, a collar rotatably mounted about the needle hub, and a needle sheath removably attached to the collar for covering the needle extending from the needle hub. Moreover, the inventive apparatus includes a housing connected to the collar and pivotable to a position substantially in alignment along the longitudinal axis of the needle hub for covering the needle after the needle sheath is removed from the collar.

BRIEF DESCRIPTION OF THE FIGURES

The present invention will become apparent and the invention itself will be best understood with reference to the following description of an embodiment of the present invention taken in conjunction with the accompanying drawings, wherein:

FIG. 1 is a perspective view of the different components of the instant invention needle protection assembly;

FIG. 2 is a perspective view of the needle hub of the instant invention;

FIG. 3 is a perspective view of the needle protection housing and the collar to which it is connected for the needle protection assembly of the instant invention;

FIG. 4 is another view of the needle protection housing and the collar to which it is attached;

FIG. 5 is yet another view of the needle protection housing and the collar to which it is attached;

FIG. 6 is a plan view of the needle protection housing and the collar to which it is attached;

FIG. 7 is a perspective view of the needle sheath of the needle protection assembly of the instant invention;

FIG. 8 is a view to the interior of the needle sheath of FIG. 7;

FIG. 9 is semi-cut away view of the fully assembled needle protection assembly of the instant invention;

FIG. 10 is a cross-sectional view of the instant inventive needle protection assembly; and FIG. 11 is a perspective view of the fully assembled needle protection assembly of the instant invention.

DETAILED DESCRIPTION OF THE INVENTION

With reference to FIG. 1, the needle protection assembly is shown to include a needle hub 2 and a needle protection housing 4 to which is connected a collar 6. The needle protection assembly further includes a needle sheath 8 that is to be removably connected to collar 6 for covering needle 10 prior to the latter's use.

With reference to FIG. 2, needle hub 2 is shown to have a proximal portion 12 and a distal portion 14. The needle hub 2 is cylindrical in shape with proximal portion 12 having a greater circumference than distal portion 14. As shown, at the proximal end at proximal portion 12 there is a luer adaptable fitting 16 for mating with luer lock type end of a syringe. Of course, if a syringe is a slip fit type syringe, then luer end 16 of needle hub 2 could slip fit over the luer end of the syringe. Simply put, Luer end 16 is ISO standard so that needle hub 2 is matable with a conventional luer of a syringe, or other similarly luered devices.

Further shown at proximal end 12 of needle hub 2 are a plurality of flanges, divided into a first set of upper flanges 18 and a second set of lower flanges 20. Flanges 20a and 20b extend orthogonally from the body of needle hub 2, and act as a retainer base for collar 6. The upper or the first set of flanges 18 also extend transversely from the body of needle hub 2 at the fore section of proximal portion 12. There are four flanges 18a-18d in the exemplar needle hub 2 shown in FIG. 2. The top surfaces 22a-22d of each of the first flanges 18a-18d are beveled, or chamfered as shown, so as to allow collar 6 to be more readily press-fitted past flanges 18a-18d onto the space 24 defined by flanges 18 and 20. The back surfaces 26a-26d of flanges 18a-18d, respectively, are flat, so that once collar 6 is fitted into space 24, it no longer could be removed therefrom. A groove 28 is formed adjacent to the underside of back surfaces 26a-26d of flanges 18a-18d, respectively, to effect a right angled relationship between surfaces 26 and the body of needle hub 2 to minimize the play between collar 6 and the retention flanges. The interior diameter of collar 6, as will be described later, is configured such that even though collar 6 is retained within space 24, it nonetheless is rotatable about needle hub 2. Element 30 is a remnant from the injection molding process of needle hub 2, as needle hub 2 may be made of ABS plastic, which is a styrene type plastic.

Distal portion 14 of needle hub 2 may also be referred to as the neck of the needle hub. A plurality of arms or stubs, shown as three exemplar sets, extend transversely from distal portion 14 of needle hub 2. A first set of arms 32a-32d are formed at the proximal end of distal portion 14. A second set of arms 34a-34c are formed at the mid section of distal portion 14. The first and second sets of arms 34 and 32 are in alignment with each other so that a number of v-shaped slots 36a, 36b and 36c are formed by aligned arms 32 and 34. As will be discussed later, These v-shaped slots or channels are to be fitted with a spline integral of needle sheath 8 for rotation purposes. Additional arms or stubs 38a and 38b are provided at the distal end of distal portion 14 of the needle hub 2. Arms 38a and 38b are used as stops for coacting against an integral spline in housing 4. The orientation of the respective sets of arms 32, 34 and 38, relative to distal portion 14 of needle hub 2, are such that slots 36a-36c are oriented not to interfere with arms 38a and 38b. A needle such as 10 shown in FIG. 1, extends from distal end 40 of needle hub 2. As shown in FIG. 1, needle hub 2 has a longitudinal axis 13.

With reference to FIG. 3-6, needle protection housing 4 and collar 6 to which it is connected are hereby described. As shown, collar 6 is cylindrical in shape and has a proximal portion or end 42 and a distal portion or end 44. Distal end 44 of collar 6 is shown to have a plurality of catch fingers or retainers 46 and two slots or channels 48 to provide additional flexibility thereat for facilitating the insertion and removal of needle sheath 8. As best shown in FIG. 4, a plurality of protrusions 50a-50d are provided at proximal end 42 of collar 6. Protrusions 50a-50d are dimensioned such that they would fit into space 24 (FIG. 2) of needle hub 2, as defined by flanges 18 and 20, to allow collar 6 to be rotatable about needle 2. For the exemplar embodiment, collar 6 is fitted to needle hub 2 via the direction shown by directional arrow 52 in FIG. 3 and directional arrow 54 in FIG. 2. Thus, as collar 6 is press-fitted onto needle hub 2, due to the beveled surfaces 22 of flanges 18 and the characteristics of the plastics material from which collar 6 and needle hub 2 are made, collar 6 is readily press-fitted over flanges 18 to settle into space 24, as its forward movement is stopped by retainer flanges 20a and 20b. Once fitted onto space 24, collar 6 remains movably coupled to proximal portion 12 of needle hub 2. To further enhance the fitting of collar 6 to needle hub 2, a portion 56 of collar 6 (FIG. 3), along with a not shown portion on the other side of collar 6, are thinned, so that extra flexibility is provided at distal end 42 of collar 6 to enhance the press or snap fitting of collar 6 over retainer flanges 18 for retention within space 24 of needle hub 2.

Connected to collar 6, by a hinge 58, is a needle protection housing 4. Hinge 58 is a newly designed living hinge that has a widened bent area 60, as well as groove 62 to enable needle housing 4 to be pivoted a great number of times relative to collar 6 without breaking off.

Needle protection housing 4 has an open proximal end 64 and a closed end 66. Housing 4 is cylindrical in shape and has an opening 68 (FIGS. 4 and 6) through which needle 10 passes, when housing 4 is pivoted toward collar 6 for covering needle 10, after needle sheath 8 has been removed from collar 6. Opening or channel 68 is formed by two lips or flaps 70 and 72 each of which extends longitudinally along substantially the entire length of housing 4. Lip 40 is shown to overlap lip 72. The overlapping is such that the combination of lips 70 and 72 provides a trap door for needle 10. Once needle 10 enters fully into housing 4, after passing lips 70 and 72, it is prevented from coming out of housing 4.

Opening 68, due to its formation by lips 70 and 72, is off centered to one side of housing 4. To enhance the entry of needle 10 into the housing 4, as best shown in FIGS. 4-6, each of lips 70 and 72 is angled, by a series of complex angles, toward the interior of housing 4. The respective angles of each of the lips would therefore vary along the length of the housing for guiding needle 10 into housing 4, along the path as shown by dotted line 74, into the interior of housing 4 via opening 68. The respective progressively angled surfaces of lips 70 and 72 are designated 71 and 73, respectively (FIG. 4). Given that the entry of needle 10 into housing 4 is guided by lips 70 and 72, the angled entry of needle 10 into housing 4 is effected in a smooth manner to substantially eliminate the possibility that contaminated fluid that remains on the needle may be flickered or splattered, when the needle comes into contact with housing 4.

As best shown in FIGS. 5 and 6, a spline 76 is integrated to and extends from the back inner surface of needle protection housing 4. After needle 10 has fully entered into housing 4, spline 76 would coact against at least one of the arms 38a and 38b, so that if needle housing 4 is turned, needle hub 2 likewise is rotated due to the rotational motion imparted to needle hub 2 by the coaction of spline 76 and arms 38. Instead of having only two arms, the set of arms or stubs 38 may have a number of arms, such as for example the same number as arms 32 and 34. For the embodiment of the instant invention, arms 38 act as a catch for integral spline 76 so that needle hub 2 is rotated in synchronization with the turning of needle protection housing 4.

To ensure that needle protection housing 4 would remain fixedly retained along the longitudinal axis 13, a lock mechanism is provided at the proximal end 64 of needle housing 4 and the exterior surface of collar 6. This ensures that once needle housing 4 is pivoted to the position along longitudinal axis 13, it will remain in alignment thereat. This lock mechanism is shown in FIGS. 3-6 as two apertures 78a and 78b at the base of needle housing 4, and two corresponding one-way catch members 80a and 80b at collar 6. When needle protection housing 4 is pivoted along the longitudinal axis 13, aperture 78a and 78b will snap fit over the one-way catch members 80a and 80b, respectively. The base surfaces 82a and 82b of one-way catch members 80a and 80b, respectively, act against top surfaces 84a and 84b at the base of apertures 78a and 78b, respectively, to fixedly retain housing 4 relative to collar 6.

Needle sheath 8 is described herein with reference to FIGS. 7 and 8. As shown, needle sheath 8 has an open base 84 at its proximal end and is closed at its distal end. Sheath 8 may be made of polypropylene that is clear, or glass so as to enable the user to visually view needle 10, when needle sheath 8 is removably coupled to collar 8. To achieve coupling to collar 6, a rim or groove 86 is formed at sheath 8 between base 84 and a circumferential shoulder 88. A number of finger grip extensions 90 formed along the longitudinal exterior surface of needle sheath 8 enable the user to readily grip needle sheath 8. When inserted to collar 6, as indicated by directional arrow 92 (FIG. 1), the open end of needle sheath 8, i.e., base 84, first makes contact with the internal fingers 46 of collar 6. Since the respective top surfaces 47 of fingers 46 are beveled and slots or channels 48 are provided at distal end 44 of collar 6, needle sheath 8 is readily inserted into the distal end 44 of collar 6, with fingers 46 of collar 6 grasping rim 86 of needle sheath 8. Circumferential shoulder 88 of sheath 8 is designed to have a dimension that enables it to seat onto edge 45 of the distal end 44 of collar 6. As a consequence, needle sheath 8 is coupled to collar 6, and more particularly to distal end 44 of collar 6, with fingers 46 gripping base 84 at rim 86. The coupling of needle sheath 8 to collar 6 is such that sheath 8 is prevented from separating accidentally from collar 6, and yet sheath 8 is readily removable from collar 6, if a predetermined force is applied in the direction opposite to that shown by directional arrow 92.

To enable collar 6 to be rotated in synchronization with needle sheath 8, two integral splines 92a and 92b extend from the inner wall of needle sheath 8. These splines coact with slots 36 to thereby enable the rotating of needle hub 2, by the turning of needle sheath 8. FIGS. 9 and 10 are cross sectional views showing needle sheath 8 removably coupled to collar 6, and collar 6 fitting to needle hub 2. FIG. 11 is a perspective view illustrating the needle protection assembly fully assembled and ready for shipment.

In operation, a user removes needle sheath 8 by applying a predetermined, or greater, force in the direction opposite to that of the directional arrow 92 (FIG. 1). Once exposed, needle 10 may be used. After use, needle protection housing 4 is pivoted to the direction of longitudinal axis 13 so that the contaminated needle enters into housing 4 and is trapped inside housing 4 by the trap door formed by the two lips. At the same time, at the alignment position along the longitudinal axis 13, housing 4 is fixedly retained to collar 6 by the mating of apertures 78 to one-way catch members 80. To remove needle hub 2 from the syringe, housing 4 is rotated to cause spline 76 extending from the back inner surface of housing 4 to act against at least one of the arms extending from the needle hub 2. Once needle hub 2 is removed from the syringe, the needle protection assembly could be properly disposed.

The invention claimed is:

1. In combination, a needle hub having a length extending along a longitudinal axis and including a proximal portion and a distal portion, at least one set of arms extending circumferentially about a given section at the distal portion of said needle hub, each pair of the circumferentially extending adjacent arms forming a slot at the given section of the distal portion of said needle hub, a needle extending from said distal portion of said hub along a longitudinal axis of said hub, a collar rotatably mounted about said needle hub, said collar having at the inner surface of its distal portion at least one retainer, a sheath having at least one internal spline fittable to a slot of a pair of adjacent arms of said one set of arms, said sheath being an enclosed sheath except for one open end, a rim formed circumferentially proximate to the open end at the outer surface of said sheath, said sheath being removably connected to said collar through the open end and by the non-permanent holding of the rim by the retainer for covering said needle prior to its use, a housing having an off centered longitudinal opening connected to said collar and pivotable to a position substantially in alignment along said longitudinal axis for covering said needle after removal of said needle sheath from said collar.

2. Combination of claim 1, wherein said needle hub comprises flange means provided spaced apart along the length of said proximal portion for retaining said collar, and wherein when said sheath is connected to said collar, the spline of said needle sheath is fitted into said slot so that said needle hub may be threadingly coupled to a luer of a syringe by rotating said needle sheath.

3. Combination of claim 2, wherein said needle hub further comprises a catch provided at said distal portion, said housing having an internal spline that coacts against said catch after said housing has been pivoted to cover said needle so that said needle hub is rotated in synchronization with the rotation of said housing, said needle hub removable from a luer end of a syringe to which it is coupled by rotating said housing.

4. Combination of claim 2, wherein said flange means comprises two sets of flanges each circumferentially extending from a different section of the proximal portion and positioned spaced apart along the length on the proximal portion of said needle hub, and wherein said collar has at the inner surface of its proximal portion a plurality of protrusions, said protrusions fitting between said spaced apart flanges when said collar is fitted about said needle hub, said collar rotatable about said needle hub.

5. Combination of claim 1, wherein said opening along said housing is formed by first and second lips each extending substantially along the length of said housing, said first lip overlapping a portion of said second lip with said opening being off centered, each of said lips being angled toward the interior of said housing with the respective angles of said lips being varied along the length of said housing, wherein when said housing is pivotally moved relative to said collar to cover said needle, said needle is guided by said lips to smoothly enter into said housing, said needle not removable from said housing once said needle has fully entered into said housing.

6. Combination of claim 1, wherein said collar has formed at its outer surface at least two catch members and wherein said housing has formed at its proximal end at least two corresponding apertures, said catch members matingly coupled to said apertures to fixedly retain said housing to said collar when said housing is pivoted to said longitudinal axis to cover said needle.

7. Apparatus, comprising:
a needle hub having a length along a longitudinal axis and a needle extending from one of its ends, said needle hub including a proximal portion and a distal portion, first set of circumferential flanges extending transversely about a section of the proximal portion, and at least first and second sets of arms extending circumferentially about respective sections along the length of the distal portion transversely from the distal portion;
a collar rotatably mounted about said needle hub adjacent to said first set of circumferential flanges and away from said first and second sets of arms; and
an enclosed needle sheath with only one open end having one internal spline formed at its inner surface removably attached to said collar through the open end for covering said needle extending from said needle hub prior to its use, said one spline fitted to a slot formed by said first and second sets of arms so that said hub is rotatable in the same direction in unison with said sheath when said sheath is attached to said hub;
wherein said collar comprises a proximal portion having at least one protrusion at its interior surface and wherein said hub comprises a space formed by spaced flanges extending transversely from its proximal portion, said collar rotatably mounted about said needle hub with said protrusion fitted within said space.

8. Apparatus of claim 7, further comprising:
a housing connected to said collar and pivotable to a position substantially in alignment along the longitudinal axis of said needle hub for covering said needle after said needle sheath has been removed from said collar, said housing having other internal spline positioned between adjacent arms of an other set of arms, the other set of arms acting as stops for said other spline so that said hub is rotatable in unison with said housing in the same direction after said housing is pivoted to the alignment position.

9. Apparatus of claim 8, wherein said collar has formed at its outer surface a first lock mechanism and wherein said housing has formed at its proximal end a second lock mechanism, said first and second lock mechanisms coacting to fixedly retain said housing to said collar once said housing is pivoted to said position to cover said needle.

10. Apparatus of claim 9, wherein said first lock mechanism comprises at least one one way catch member extending from the outer surface of said collar, and said second lock mechanism comprises at least one corresponding aperture at said housing, said one way catch member matingly coupled to said aperture for fixedly retaining said housing to said collar when said housing is pivoted to cover said needle.

11. Apparatus of claim 7, wherein said sheath has a rim formed circumferentially proximate to the open end of said sheath, and wherein said collar has a distal end having retainers thereat, the rim being held by the retainers when said sheath is connected to said collar.

12. Apparatus of claim 7, wherein said proximal portion of said needle hub has a luer end for mating to a syringe and said distal portion of said needle hub has said needle extending therefrom.

13. A needle hub comprising a proximal portion and a distal portion extending along a length along a longitudinal axis, first plurality and second plurality of flanges transversely extending circumferentially from respective sections along the length of said proximal portion, said first and second plurality of flanges being spaced apart to define a circumferential space along the length at said proximal portion of said needle hub whereat a collar is rotatably mounted about and between said first plurality and second plurality of flanges, at least a first set of arms extending circumferentially and transversely from a section along the length of the distal portion of said needle hub for forming at least one slot by at least a pair of adjacent arms for accepting a spline formed at the internal surface of an enclosed needle sheath with one open end when said sheath is coupled to said collar through the open end for covering a needle extending from said needle hub prior to use, and a second set of arms extending circumferentially and transversely from another section of the distal portion of said needle hub to catch a spline formed at the internal surface of a housing pivotally connected to said collar after said sheath has been removed from said collar and said housing has been positioned to cover the needle.

14. Needle hub of claim 13, wherein the side of each flange of one of said first and second plurality of flanges to which said collar is press fitted against for mounting to said needle hub is beveled to ease the fitting of said collar to said needle hub, said collar being retained at but rotatable about the space defined by said first and second plurality of flanges once it is press fitted past the beveled flanges.

15. Needle hub of claim 13, wherein said needle hub comprises a luer end at its proximal portion for mating to a syringe.

16. A method of making a medical needle assembly, comprising the steps of:
a) providing a needle hub having a length extending along a longitudinal axis with a proximal portion and a distal portion, sets of flanges circumferentially extending transversely from respective sections along the length of the proximal portion and first and second sets of arms extending circumferentially and transversely from respective sections along the length of the distal portion, adjacent pairs of at least one set of said arms forming respective slots;
b) extending a needle from the distal portion of said hub;
c) rotatably mounting a collar about said needle hub between said sets of flanges, said collar having at its distal end at least one retainer; and
d) attaching an enclosed needle sheath having an open end to the distal end of said collar through the open end for covering said needle prior to its use, said needle sheath having an internal spline and a circumferential rim proximate to its opening, said rim being non-permanently held by said retainer at said collar when said sheath is mated to said collar so that said sheath is removably connected to said collar.

17. Method of claim 16, wherein the spline of said sheath fits into one of the slots formed by said at least one set of arms so that said hub is rotatable in the same direction in unison with said sheath when said sheath is attached to said hub, whereby said hub is connectable to and removable from a syringe by rotating said sheath.

18. Method of claim 16, further comprising the steps of: connecting a housing to said collar; and
effecting an off centered longitudinal opening substantially along the length of said housing, said housing pivotable to a position substantially in alignment along the longitudinal axis of said needle hub for covering said needle after removal of said needle sheath from said collar.

19. Method of claim 16, wherein said step a comprises the steps of:
spacing said sets of flanges apart from each other along the length of said proximal portion;
beveling the side of each of the set of flanges to which said collar is to be press fitted against for easing the fitting of said collar onto said needle hub; and
extending at least one arm transversely from the distal portion of said needle hub to act as a catch for an internal spline of a housing pivotable from said collar to cover said needle so that said hub is rotatable in response to the rotation of said housing after said needle is covered by said housing.

20. Method of claim 16, further comprising the steps of:
forming a plurality of protrusions at the interior surface of the proximal portion of said collar; and
forming a plurality of retainers at the interior surface of the distal portion of said collar;
wherein said step c further comprises the step of:
press fitting said collar to said needle hub by fitting said protrusions to a space defined between said sets of flanges extending transversely from said needle hub, said collar rotatable about said needle hub when said protrusions are fitted about said space.

21. Method of claim 16, further comprising the steps of:
forming at the outer surface of said collar at least one catch member; and
forming at a proximal end of said housing at least one corresponding aperture;
wherein said catch member matingly couples to said aperture to fixedly retain said housing to said collar when said housing is pivoted to said longitudinal axis to cover said needle.

* * * * *